(12) United States Patent
Beckmann et al.

(10) Patent No.: US 8,649,012 B2
(45) Date of Patent: Feb. 11, 2014

(54) OPTICAL GAS SENSOR

(71) Applicant: Dräger Safety AG & Co. KGaA, Lübeck (DE)

(72) Inventors: Udo Beckmann, Stockelsdorf (DE); Livio Fornasiero, Bliestorf (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 13/736,226

(22) Filed: Jan. 8, 2013

(65) Prior Publication Data
US 2013/0265579 A1 Oct. 10, 2013

(30) Foreign Application Priority Data
Apr. 5, 2012 (DE) .......................... 10 2012 007 016

(51) Int. Cl.
*G01N 21/00* (2006.01)
(52) U.S. Cl.
USPC ............................ 356/437; 356/436; 250/366
(58) Field of Classification Search
USPC ................. 356/432–444, 71–73; 250/339.04, 250/339.07, 339.13, 338.05, 366
See application file for complete search history.

(56) References Cited

U.S. PATENT DOCUMENTS

| 5,022,045 A | * | 6/1991 | Elliott | 374/20 |
| 5,644,069 A | * | 7/1997 | Liu et al. | 73/23.2 |
| 5,866,907 A | * | 2/1999 | Drukier et al. | 250/366 |
| 6,850,013 B1 | * | 2/2005 | Ashley et al. | 315/169.1 |
| 2002/0051132 A1 | * | 5/2002 | Ohno et al. | 356/437 |
| 2005/0154562 A1 | * | 7/2005 | Matsuura et al. | 702/185 |
| 2009/0235720 A1 | | 9/2009 | Smith | |
| 2010/0007889 A1 | * | 1/2010 | Van Kesteren | 356/436 |
| 2010/0225917 A1 | * | 9/2010 | Dreyer et al. | 356/437 |

FOREIGN PATENT DOCUMENTS

| EP | 0 262 779 A1 | 4/1988 |
| WO | 2009/019467 A1 | 2/2009 |
| WO | 2012/059743 A2 | 5/2012 |
| WO | 2012/059744 A1 | 5/2012 |

* cited by examiner

*Primary Examiner* — Sang Nguyen
(74) *Attorney, Agent, or Firm* — McGlew & Tuttle, P.C.

(57) ABSTRACT

An optical gas sensor with a light-emitting diode (2), a photosensor (8), a measuring section between the light-emitting diode and the photosensor, and a control and analyzing unit (16), which is set up to determine the concentration of a gas in the measuring section from the light intensity measurement by the photosensor. The control and analyzing unit (16) is set up to measure the forward diode voltage over the light-emitting diode at a constant current, to determine the temperature of the light-emitting diode from the detected forward diode voltage over the light-emitting diode by means of a preset temperature dependence of the forward diode voltage, and to apply a correction function as a function of the light-emitting diode temperature determined, with which the measurement is converted to that of a preset temperature of the light-emitting diode.

18 Claims, 7 Drawing Sheets

OPTICAL GAS SENSOR

CROSS REFERENCE TO RELATED APPLICATIONS

This application claims the benefit of priority under 35 U.S.C. §119 of German Patent Application DE 10 2012 007 016.0 filed Apr. 5, 2012, the entire contents of which are incorporated herein by reference.

FIELD OF THE INVENTION

The present invention pertains to an optical gas sensor with a light-emitting diode, a photosensor, a measuring section between light-emitting diode and photosensor, and a control and analyzing unit, which is set up to determine the concentration of a gas in the measuring section on the basis of the measurement performed by the photosensor.

BACKGROUND OF THE INVENTION

Optical gas sensors operate with a light source (radiation source), a photosensor and a measuring section located between the light source and the photosensor. A wavelength range, in which the target gas has a characteristic absorption, can be selected with a band pass filter. Thermal light sources, such as diaphragm sources or spiral-wound filaments, lasers or light-emitting diodes (especially in the IR and UV ranges) are used as light sources. Thermal light sources emit in a very broad spectral band. However, this causes a lot of energy to flow into spectral ranges that are not used to analyze and calculate gas concentrations. Such gas sensors therefore have low efficiency in terms of their energy consumption. In addition, their output cannot be modified rapidly without additional mechanical components, which limits the use of noise suppression methods at a simultaneously fast response time.

By contrast, lasers lead mostly to a very good signal-to-noise ratio, but they are relatively expensive and must be thermally stabilized.

Light-emitting diodes (LEDs) are substantially more cost-effective than lasers and emit in a limited spectral range, so that they are more efficient in terms of their energy consumption than thermal light sources. In addition, just like lasers, LEDs lend themselves to fast electric modulation. On the other hand, the spectral emission characteristic of LEDs shows a thermal drift, which is noticeable in a disturbing manner in thermally non-stabilized optical gas sensors.

SUMMARY OF THE INVENTION

An object of the present invention is to provide an optical gas sensor, which permits accurate measurements even without thermal stabilization with an LED as a light source.

According to the invention, an optical gas sensor is provided comprising a light-emitting diode (LED), a photosensor, a measuring section between the light-emitting diode and the photosensor and a control and analyzing unit. The control and analyzing unit determines a concentration of a gas in the measuring section from a light intensity measurement by the photosensor. The control and analyzing unit measures a forward diode voltage over the light-emitting diode at a known current and determines a temperature of the light-emitting diode, from the forward diode voltage detected over the light-emitting diode, based on a preset dependence of the forward diode voltage on temperature. The control and analyzing unit applies a correction function, that is a function of the light-emitting diode temperature determined, with which the measurement is converted to that of a preset temperature of the light-emitting diode.

The control and analyzing unit is set up according to the present invention to measure the forward diode voltage over the light-emitting diode at a known current through the diode. The temperature of the light-emitting diode can be derived from the detected forward diode voltage by means of a predetermined dependence of the forward diode voltage on the temperature of the light-emitting diode. The dependence, known in advance, may be available, for example, in the form of a look-up table or a temperature characteristic calibrated in advance as a function of the forward diode voltage. The control and analyzing unit is set up, furthermore, to apply a correction function, with which the measurement is converted to a preset reference temperature, as a function of the light-emitting diode temperature determined. The concentration of the target gas in the measuring section can be determined in this manner independently from the temperature of the light-emitting diode.

In a preferred embodiment, the control and analyzing unit is set up, furthermore, to operate the photosensor alternatingly in a mode for light intensity measurement and in a temperature-measuring mode, in which a preset, constant current is applied over the photosensor and the resulting forward diode voltage over the photosensor is detected. Based on a predetermined dependence of the forward diode voltage on the temperature of the photosensor, a correction function, determined in advance, is applied to the measurement of the photosensor in the control and analyzing unit as a function of the photosensor temperature, and the measurement is converted to that of a preset temperature of the photosensor.

The present invention will be described below on the basis of examples in connection with the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
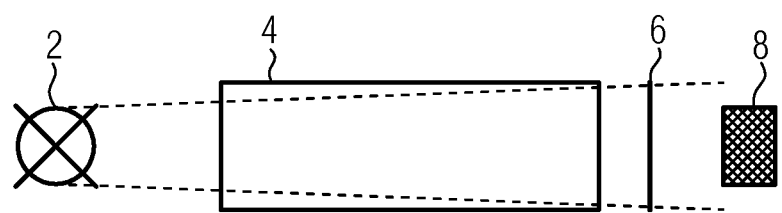
FIG. 1 is a schematic view of an optical gas sensor.

Referring to the drawings in particular, FIG. 1 schematically shows the design of an optical gas sensor. The gas sensor has a light-emitting diode 2 and a photosensor 8 in the form of a photodiode. A measuring section is located between sensor 2 and photodiode 8, a gas sample holder 4 containing the gas to be measured being shown in this example. A narrow frequency band, in which the target gas to be measured possesses characteristic spectral properties, is cut out of the wavelength spectrum, which passes through the measuring section starting from the light-emitting diode 2, by means of a band pass filter 4. The target gas may have, for example, a known high absorbing capacity in the spectral range of interest. The concentration of the target gas can thus be calculated from the determination of the absorption.

Figure 2:
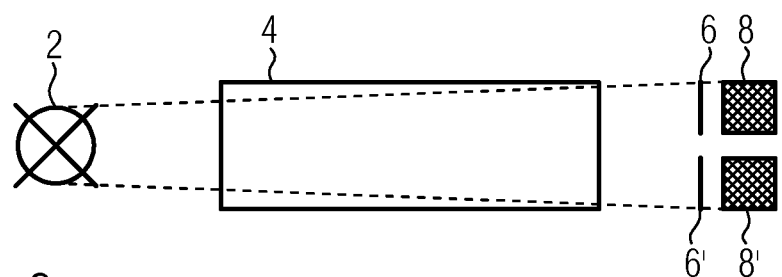
FIG. 2 is a schematic view of an alternative embodiment of the gas sensor.

FIG. 2 shows a gas sensor having a similar design, which does, however, have another photodiode 8' behind another band pass filter 6' besides a photodiode 8 behind the measuring section and a band pass filter 6. The measurement with the second photodiode 8' takes place in a reference wavelength range, and the measured signals of the photodiode 9 can then be standardized by the measured signal of photodiode 8'.

Figure 3:
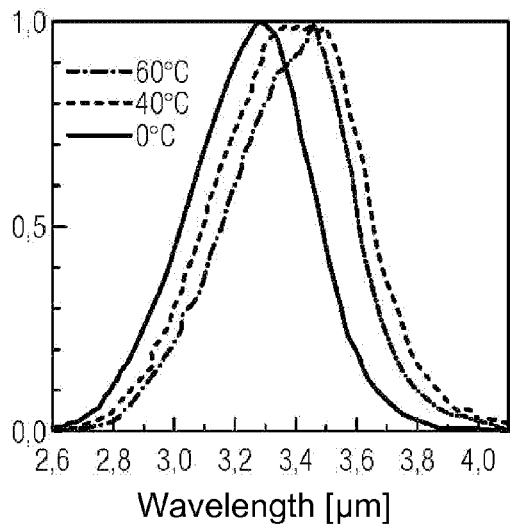
FIG. 3 is graph showing standardized emission spectra of a light-emitting diode at different temperatures.
Figure 4:
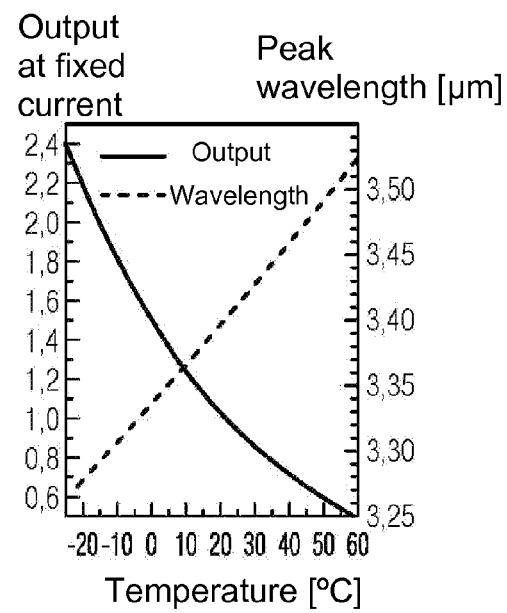
FIG. 4 is graph showing the radiation output of a light-emitting diode as a function of the temperature at a fixed current and, on the right-hand scale, the peak wavelength as a function of the temperature.

FIGS. 3 and 4 illustrate the temperature dependence of the emission of a light-emitting diode. FIG. 3 shows the standardized emission spectrum of the light-emitting diode for different temperatures. It can be seen that the peak of the emission spectrum is shifted to the right towards longer wavelengths with rising temperatures. FIG. 4 shows on the left-hand Y axis the radiation output of the light-emitting diode at a fixed current as a function of the temperature. The peak wavelength is shown as a function of the temperature on the right-hand Y axis. It becomes clear from this as well that the peak wavelength is shifted towards longer wavelengths with rising temperature, whereas the output of the photodiode decreases at fixed current with rising temperature.

Figure 8:
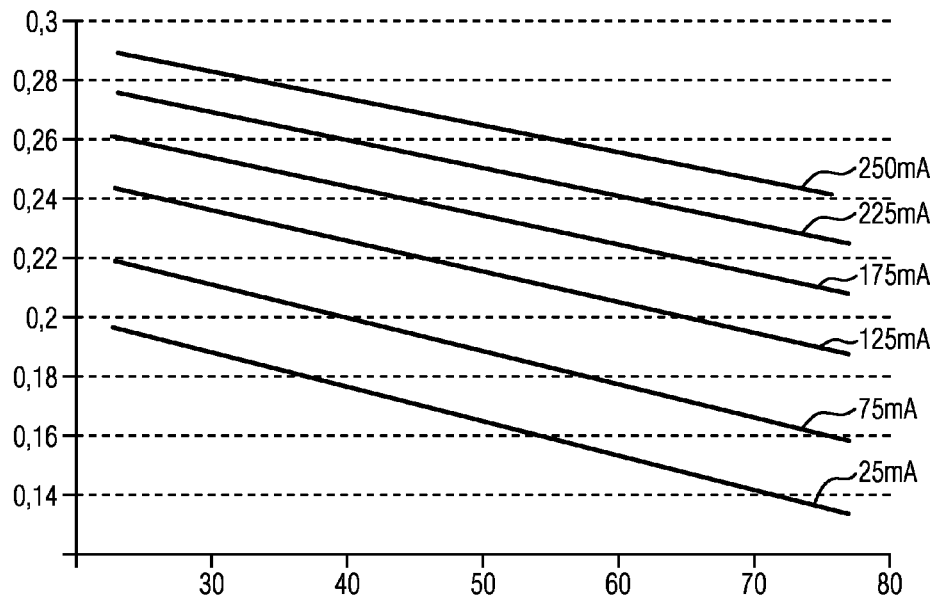
FIG. 8 is graph showing the forward diode voltage over a photodiode (PD) as a function of the temperature for different constant currents.

By measuring the forward diode voltage over the photodiode at a fixed current, the temperature of the photodiode can be determined by the dependence known in advance, which is shown in FIG. 8. Conversely, it is then possible to make a conversion to a preset temperature, for example, 20°, in case of a light-emitting diode temperature thus determined. As a result, the measurement of the intensity of the radiation of the photodiode 8 passing through the measuring section becomes independent from the temperature of the light-emitting diode 2. The light-emitting diode temperature does not have to be calculated independently as an interim result; the correction can rather also be performed directly for a preset light-emitting diode temperature.

Figure 5:
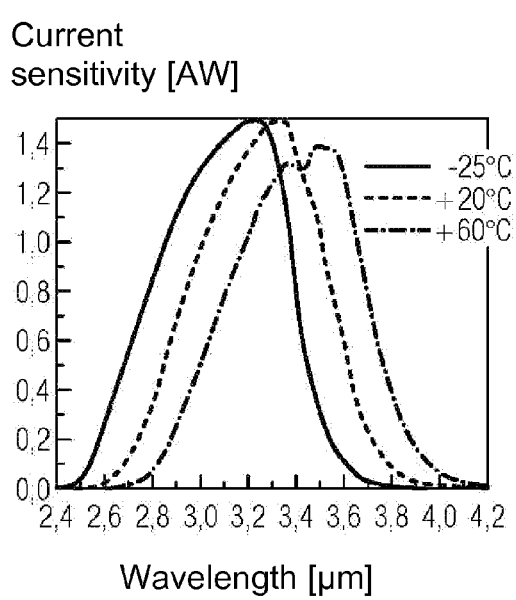
FIG. 5 is graph showing the sensitivity in a photodiode at different temperatures as a function of the wavelength.
Figure 6:
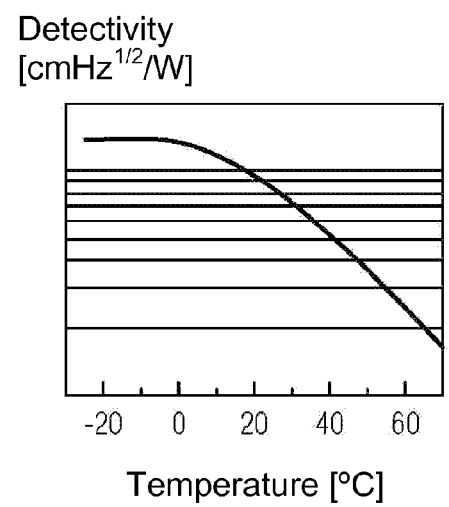
FIG. 6 is graph showing the detectivity of a photodiode as a function of temperature.

FIGS. 5 and 6 show the temperature-dependence characteristic of a photodiode as a photosensor for different temperatures. FIG. 5 shows the current sensitivity of a photodiode for different temperatures. It can be seen that the current sensitivity is shifted with rising temperature towards longer wavelengths. FIG. 6 shows the detectivity of a photodiode as a function of temperature; it is a characteristic for the signal-to-noise ratio standardized for bandwidth, detector area and incident signal intensity. It can be seen in FIG. 6 that the detectivity decreases with rising temperature, i.e., the signal value decreases relative to the noise signal of the photodiode. In an advantageous embodiment of the present invention, the photodiode can accordingly be operated in a mode for temperature measurement, in which a known current is applied to the photodiode and the forward diode voltage resulting therefrom is determined. By reversing this already known relationship, the photodiode temperature can be determined herefrom and the signal measured by the photodiode can thus be corrected for a preset temperature. It is not necessary here for the photodiode temperature to be actually calculated as an interim result; the measurement may also be converted directly to a preset temperature.

Figure 7:
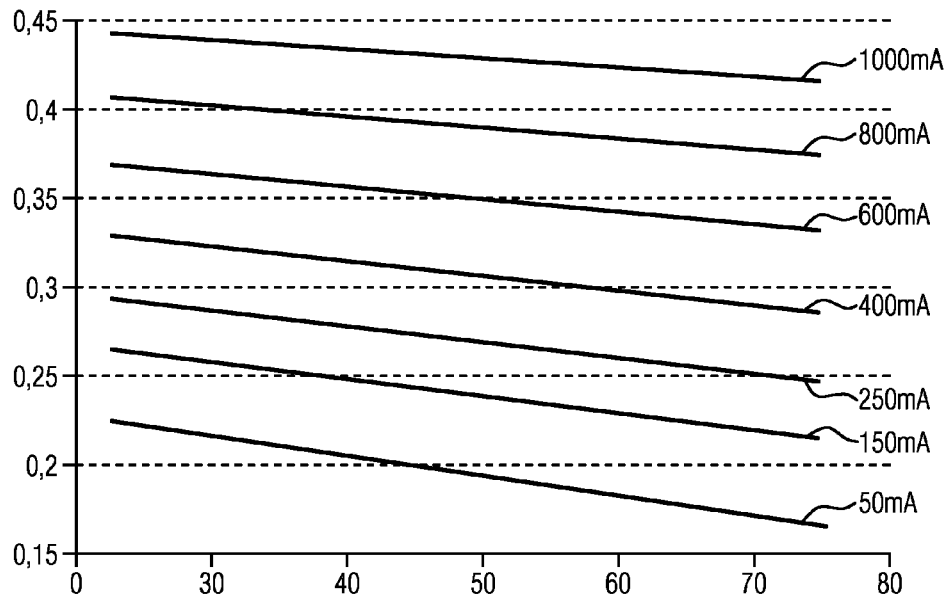
FIG. 7 is graph showing the forward diode voltage over a light-emitting diode as a function of the temperature for different constant currents.

FIG. 7 shows the forward diode voltage over the light-emitting diode as a function of temperature for different constant, preset currents. The forward diode voltage over the photodiode is correspondingly shown in FIG. 8 as a function of the temperature for different preset, constant currents. It can be seen from this that an indicator for the temperature can always be derived by determining the forward diode voltage.

Figure 9:
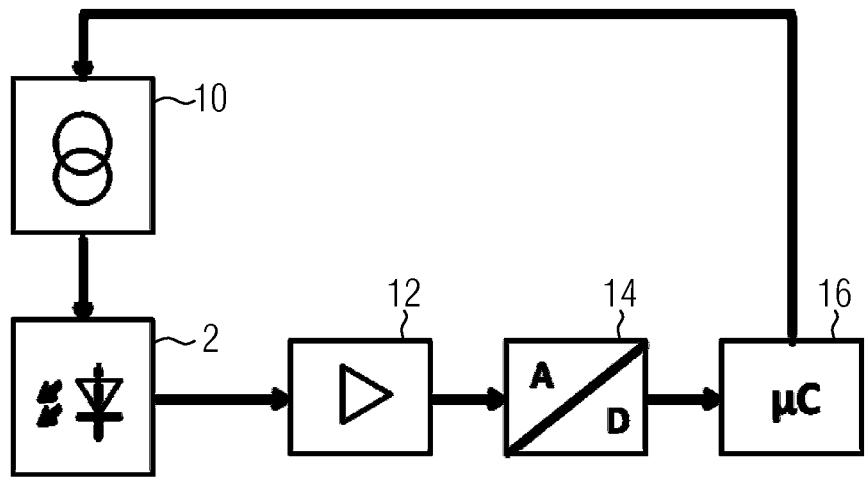
FIG. 9 is a schematic block diagram of a circuit for measuring the forward diode voltage of an LED.
Figure 10:
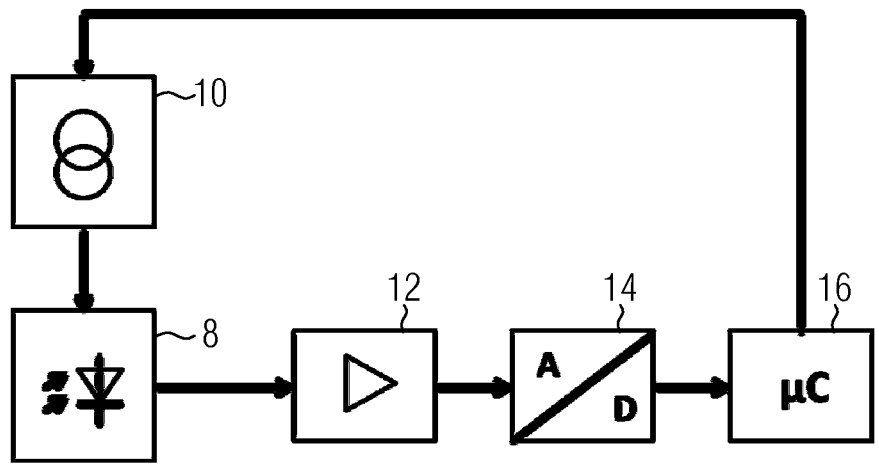
FIG. 10 is a schematic block diagram of a circuit for measuring the forward diode voltage over a photodiode at constant current.

The circuits needed for this are schematically shown in FIGS. 9 and 10. FIG. 9 shows a power source 10, which applies a known current through LED 2. The digitized measured forward diode voltage is sent to a microprocessor via an operational amplifier 12 and an analog/digital converter 14. FIG. 10 shows the corresponding circuit for measuring the forward diode voltage over a photodiode 8.

Figure 11:
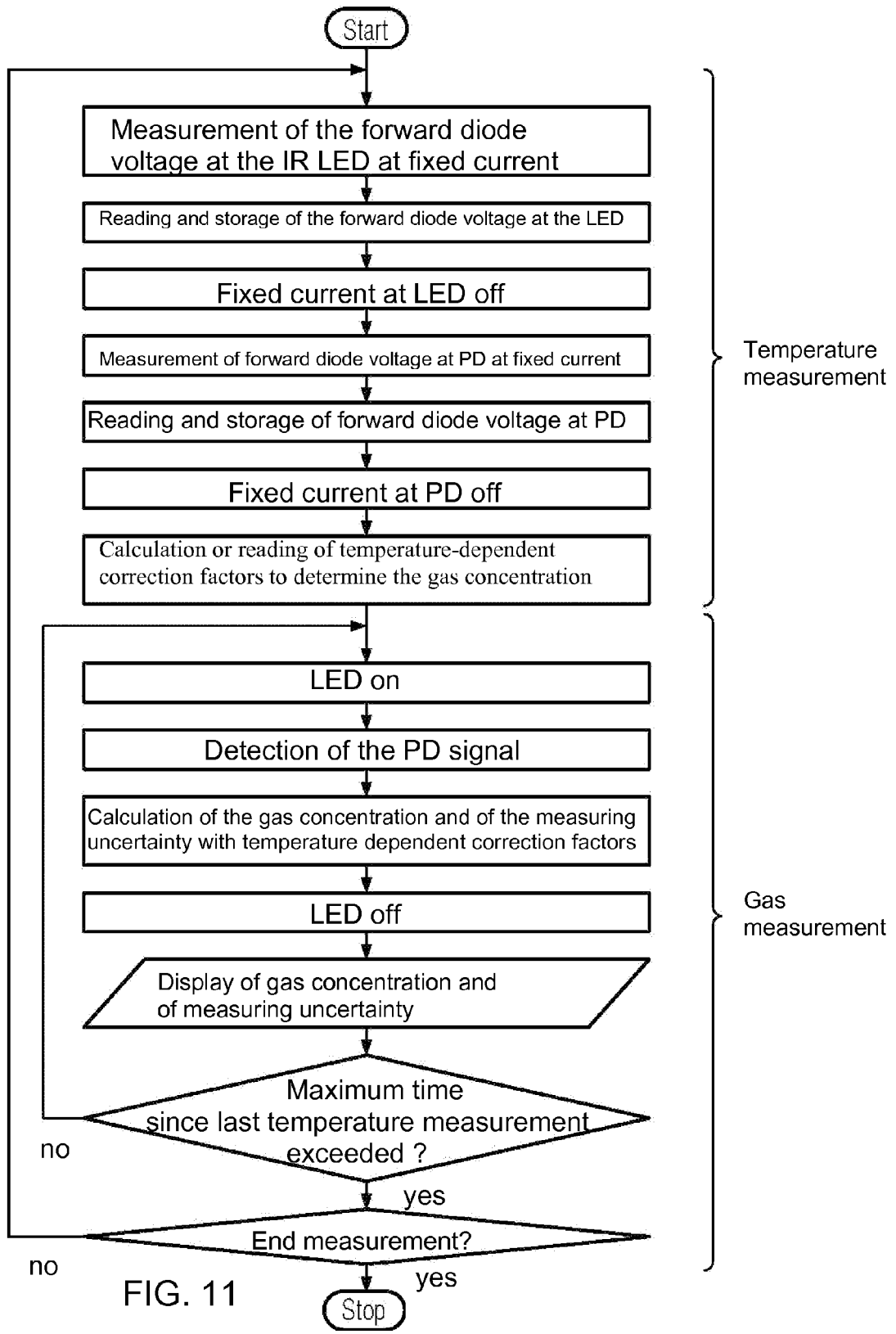
FIG. 11 is a flow chart with the sequence of steps of an optical gas sensor with temperature compensation.

FIG. 11 shows a flow chart, which illustrates a possible mode of operation of an optical gas sensor. A temperature measurement is performed at first for the light-emitting diode. A known current is first applied now over the light-emitting diode. The resulting forward diode voltage over the light-emitting diode is then measured and stored. The known current through the light-emitting diode can then be switched off again. A known current is then likewise applied through the photodiode. The resulting forward diode voltage over the photodiode is measured and stored, after which the known current through the photodiode is switched off again. Correction factors are subsequently polled from a stored table or determined according to preset dependences, and a subsequent measurement of the gas concentration is converted with these correction factors to preset temperatures of the light-emitting diode and photodiode.

This is followed by the measurement of the gas concentration, for which the light-emitting diode is switched on and the resulting photodiode signal is detected. The gas concentration is calculated from the photodiode signal with temperature-dependent corrections for the light-emitting diode temperature and the photodiode temperature. The light-emitting diode is then switched off again and the gas concentration determined is displayed. The time elapsed since the last temperature measurement is then checked. The temperature measurement may be repeated at regular or irregular intervals, for example, every 5 minutes. If the time elapsed since the last temperature measurement was performed is longer than intended, the control and analyzing unit returns to the starting point and performs a repeated temperature measurement. Otherwise, another measurement of the gas concentration will follow directly.

Figure 12:
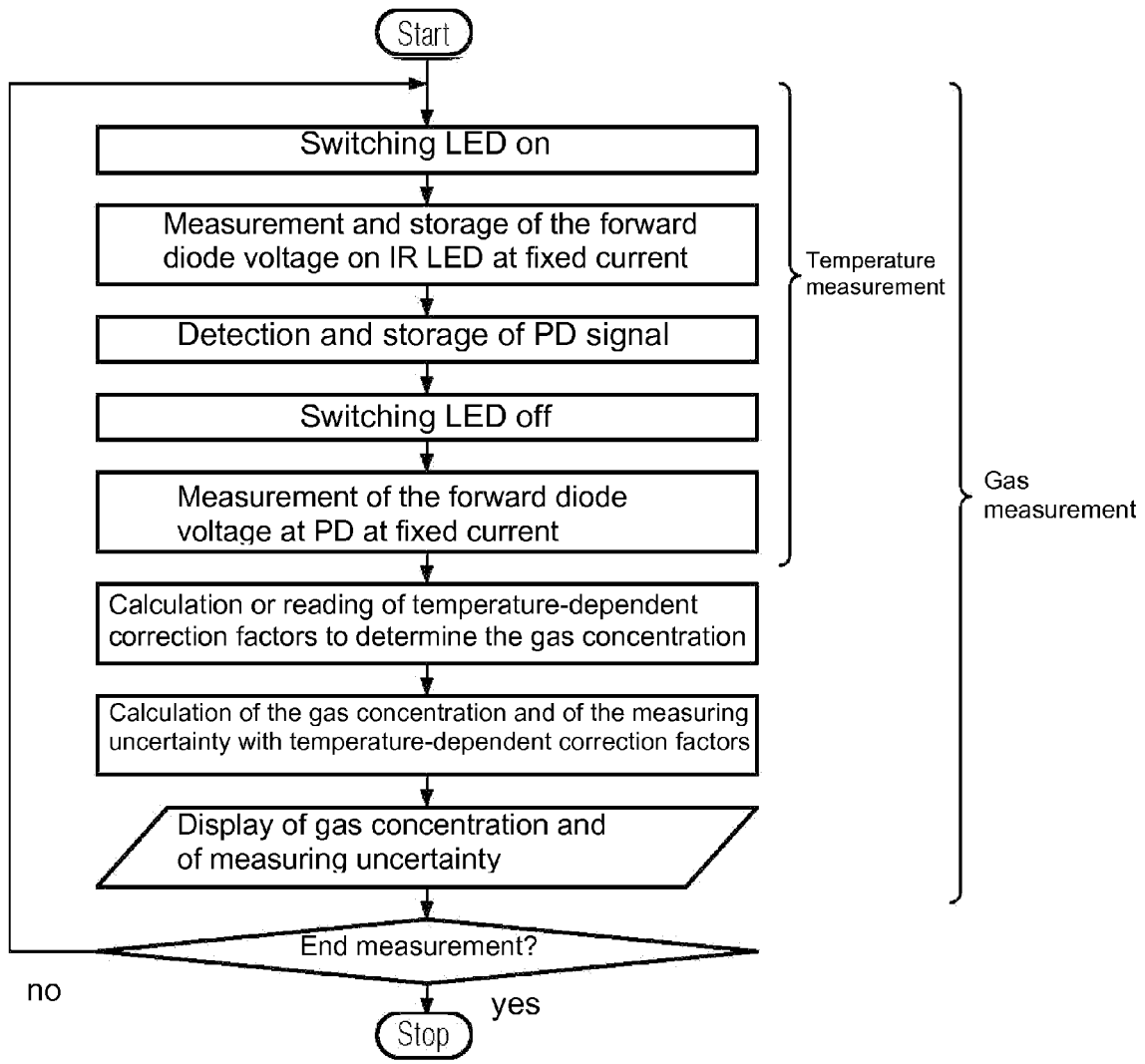
FIG. 12 is an alternative flow chart of the operation of an optical gas sensor with temperature compensation.

FIG. 12 illustrates an alternative mode of operation, in which a temperature measurement is performed before each gas measurement, unlike in the mode of operation shown in FIG. 11. The light-emitting diode is switched on at the beginning A known current is then applied over the light-emitting diode and the resulting forward diode voltage over the light-emitting diode is detected and stored. The intensity detected by the photodiode after passage through the measuring section is stored as well. After switching off the light-emitting diode, a constant current is applied over the photodiode and the resulting forward diode voltage over the photodiode is measured. Correction factors, which are to be applied to the measurement of the gas concentration in order to standardize the measurement to a preset temperature of the light-emitting diode and photodiode (e.g., the temperature at which the system with the light-emitting diode and photodiode was calibrated), are then read or determined as a function of the temperature of the light-emitting diode and the temperature of the photodiode.

Figure 13:
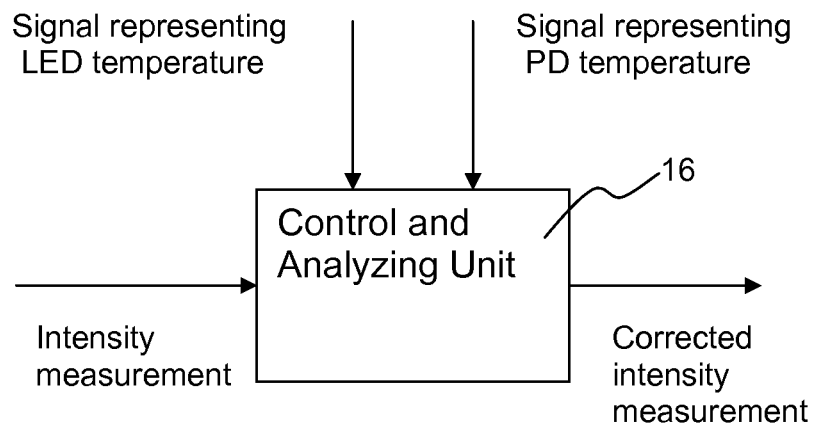
FIG. 13 is a schematic block diagram of the control and analyzing unit showing the output of a corrected measurement signal based on a correction function.

FIG. 13 schematically illustrates the control and analyzing unit 16 applying correction factors to the measurement of the gas concentration. In particular, the intensity measurement is received from the PD 8 and a correction function is applied to provide a corrected intensity measurement as an output. The correction function is a function of the light-emitting diode temperature determined and/or the photo diode temperature determined. This is shown as a signal representing LED temperature and as a signal representing PD temperature. The corrected intensity measurement is a measurement of gas concentration based on the relationship established during calibration at a preset temperature.

Besides displaying the gas concentration determined, a measuring uncertainty can also be determined with temperature-dependent correction factors and displayed. The already known measuring uncertainty of the gas concentration at the reference temperature is multiplied for this by two correction factors. One correction factor is the quotient of the emitted radiation output of the LED in the wavelength range of gas absorption at the reference temperature to the emitted radiation output of the LED in the wavelength range of gas absorption at the measured temperature. The other correction factor is the quotient of the detectivity of the detector in the wavelength range of gas absorption at the reference temperature to the detectivity of the detector in the range of gas absorption at the measured temperature. The measuring uncertainty of the device can also be measured at different temperatures and stored in a look-up table.

Figure 14:
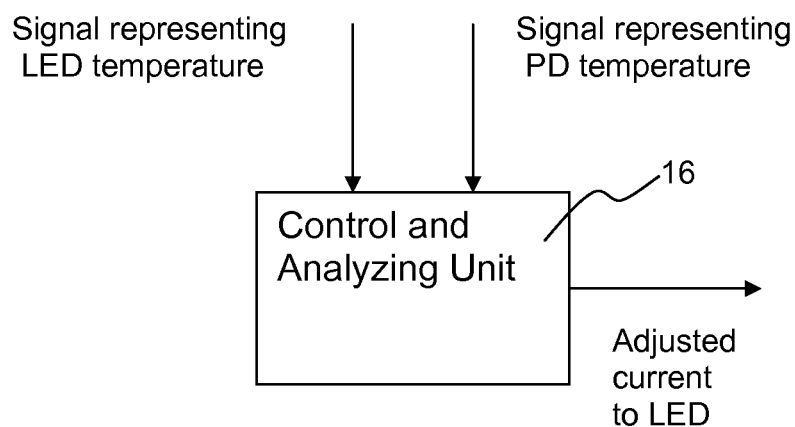
FIG. 14 is a schematic block diagram of the control and analyzing unit showing the control of the current to the LED (adjusted current) based on the signal representing LED temperature and the signal representing PD temperature.

The measuring uncertainty increases markedly with rising temperature based on the above explanations. The increase in measuring uncertainty with rising temperature can be reduced in an advantageous embodiment (FIG. 14). The radiation output of the LED, with decreases with rising temperature (FIG. 4), can be adjusted for this to a fixed radiation output, e.g., at the reference temperature. This adjustment is based on an increase in the LED current with rising temperature. The necessary LED current can be determined, for example, by means of a look-up table or a functional equation and is adjusted by means of the control and analyzing unit 16.

In another advantageous embodiment (FIG. 14), the reduction of the detectivity of the photosensor with rising temperature is compensated by an excessive increase in the radiation output of the LED. Not only is the radiation output of the LED maintained at a constant value but even increased further with rising temperature. This likewise happens by means of an increase in the LED current. The necessary value of the current can likewise be determined by means of a look-up table or a functional equation and adjusted by means of the control and analyzing unit 16.

While specific embodiments of the invention have been shown and described in detail to illustrate the application of the principles of the invention, it will be understood that the invention may be embodied otherwise without departing from such principles.

APPENDIX

List of Reference Numbers

2 Light-emitting diode
4 Gas sample holder
6 Band pass filter
8 Photodiode
10 Power source
12 Operational amplifier
14 Analog/digital converter
16 Control and analyzing unit

What is claimed is:

1. An optical gas sensor comprising:
a light-emitting diode;
a photosensor;
a measuring section between the light-emitting diode and the photosensor; and
a control and analyzing unit determining a concentration of a gas in the measuring section from a light intensity measurement by the photosensor, the control and analyzing unit measuring a forward diode voltage over the light-emitting diode at a known current and determining a temperature of the light-emitting diode from the forward diode voltage detected over the light-emitting diode based on a preset dependence of the forward diode voltage on temperature, and applying a correction function that is a function of the light-emitting diode temperature determined, with which the measurement is converted to that of a preset temperature of the light-emitting diode, the control and analyzing unit reducing measuring uncertainty, which increases with rising temperature of the LED, by adjusting a radiation output of the LED to a preset constant radiation output.

2. An optical gas sensor in accordance with claim 1, wherein:
the photo sensor is a photodiode; and
the control and analyzing unit operates the photodiode alternatingly in a mode for light intensity measurement and in a temperature-measuring mode, in which a preset current is applied to the photodiode and the resulting forward diode voltage over the photodiode is detected in order to apply, due to a preset temperature dependence of the forward diode voltage, a correction function that is a function of the photodiode temperature, with which the measurement is converted to that of a preset temperature of the photodiode.

3. An optical gas sensor in accordance with claim 1, wherein the photosensor comprises one of a photodiode, a thermopile, a pyroelectric element and a photoacoustic measuring cell.

4. An optical gas sensor in accordance with claim 1, wherein the control and analyzing unit reduces measuring uncertainty, which increasing with rising temperature of the photosensor, by increasing the radiation output of the LED to an extent that a decreasing detectivity of the photosensor is compensated thereby.

5. An optical gas sensor in accordance with claim 1, wherein:
said control and analyzing unit increases current to said light-emitting diode with rising temperature of said photosensor to compensate for decreasing detectivity of said photosensor with said rising temperature of said photosensor.

6. An optical gas sensor comprising:
a light-emitting diode;
a photosensor;
a measuring section between the light-emitting diode and the photosensor; and
a control and analyzing unit determining a concentration of a gas in the measuring section from a light intensity measurement by the photosensor, the control and analyzing unit measuring a forward diode voltage over the light-emitting diode at a known current and determining a temperature of the light-emitting diode from the forward diode voltage detected over the light-emitting diode based on a preset dependence of the forward diode voltage on temperature, and applying a correction function that is a function of the light-emitting diode temperature to standardize the measurement to that of a preset temperature of the light-emitting diode, said control and analyzing unit increasing current to said light-emitting diode with rising temperature of said photosensor to compensate for decreasing detectivity of said photosensor with said rising temperature of said photosensor.

7. An optical gas sensor in accordance with claim 6, wherein:
the photo sensor is a photodiode; and
the control and analyzing unit operates the photodiode alternatingly in a mode for light intensity measurement and in a temperature-measuring mode, in which a preset current is applied to the photodiode and the resulting forward diode voltage over the photodiode is detected in order to apply, due to a preset temperature dependence of the forward diode voltage, a correction function that is a function of the photodiode temperature determined to standardize the measurement to that of a preset temperature of the photodiode.

8. An optical gas sensor in accordance with claim 6, wherein the photosensor comprises one of a photodiode, a thermopile, a pyroelectric element and a photoacoustic measuring cell.

9. An optical gas sensor in accordance with claim 6, wherein the control and analyzing unit reduces measuring uncertainty, which increases with rising temperature of the LED, by adjusting a radiation output of the LED to a preset constant radiation output.

10. An optical gas sensor in accordance with claim 6, wherein the control and analyzing unit reduces measuring uncertainty, which increasing with rising temperature of the photosensor, by increasing the radiation output of the LED to an extent that a decreasing detectivity of the photosensor is compensated thereby.

11. An optical gas sensor in accordance with claim 6, wherein:
said control and analyzing unit increases current to said light-emitting diode with rising temperature of said light-emitting diode to reduce measuring uncertainty of the optical gas sensor.

12. An optical gas sensor comprising:
a light-emitting diode;
a photosensor;
a measuring section between the light-emitting diode and the photosensor;
a control and analyzing unit receiving a light intensity measurement signal from the photosensor, the control and analyzing unit receiving a light-emitting diode forward diode voltage signal corresponding to a temperature of the light-emitting diode based on a preset dependence of the forward diode voltage on temperature, and determining a concentration of a gas in the measuring section from a light intensity measurement by compensating for changes in temperature of the light-emitting diode from a gas sensor calibration temperature;
the photo sensor is a photodiode; and
the control and analyzing unit operates the photodiode alternatingly in a mode for light intensity measurement and in a temperature-measuring mode, in which a preset current is applied to the photodiode and the resulting forward diode voltage over the photodiode is detected in order to apply, due to a preset temperature dependence of the forward diode voltage, a correction function that is a function of the photodiode temperature, with which the measurement is converted to that of a preset temperature of the photodiode.

13. An optical gas sensor in accordance with claim 12, wherein the compensating comprises applying a correction function to the light intensity measurement, which correction function is a function of the light-emitting diode temperature determined, to form a light intensity measurement that corresponds to a light intensity measurement at a preset temperature for the concentration of a gas present in the measuring section.

14. An optical gas sensor in accordance with claim 13, wherein the photosensor comprises one of a photodiode, a thermopile, a pyroelectric element and a photoacoustic measuring cell.

15. An optical gas sensor in accordance with claim 12, wherein the compensating comprises reducing measuring uncertainty, which increases with rising temperature of the LED, by adjusting a radiation output of the LED to a preset constant radiation output.

16. An optical gas sensor in accordance with claim 12, wherein the compensating comprises reducing measuring uncertainty, which increasing with rising temperature of the photosensor, by increasing the radiation output of the LED to an extent that a decreasing detectivity of the photosensor is compensated thereby.

17. An optical gas sensor in accordance with claim 12, wherein:
said control and analyzing unit increases current to said light-emitting diode with rising temperature of said photosensor to compensate for decreasing detectivity of said photosensor with said rising temperature of said photosensor.

18. An optical gas sensor comprising:
a light-emitting diode;
a photosensor;
a measuring section between the light-emitting diode and the photosensor; and
a control and analyzing unit determining a concentration of a gas in the measuring section from a light intensity measurement by the photosensor, the control and analyzing unit measuring a forward diode voltage over the light-emitting diode at a known current and determining a temperature of the light-emitting diode from the forward diode voltage detected over the light-emitting diode based on a preset dependence of the forward diode voltage on temperature, and applying a correction function that is a function of the light-emitting diode temperature determined, with which the measurement is converted to that of a preset temperature of the light-emitting diode;

the photo sensor is a photodiode; and the control and analyzing unit operates the photodiode alternatingly in a mode for light intensity measurement and in a temperature-measuring mode, in which a preset current is applied to the photodiode and the resulting forward diode voltage over the photodiode is detected in order to apply, due to a preset temperature dependence of the forward diode voltage, a correction function that is a function of the photodiode temperature, with which the measurement is converted to that of a preset temperature of the photodiode.

* * * * *